(12) United States Patent
Roeper et al.

(10) Patent No.: US 8,129,195 B2
(45) Date of Patent: Mar. 6, 2012

(54) METHOD FOR THE PRODUCTION OF AN ANALYTICAL ELEMENT

(75) Inventors: Josef Roeper, Neuhofen (DE); Werner Finke, Einhausen (DE); Beate Koschorreck, Schriesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 75 days.

(21) Appl. No.: 12/651,863

(22) Filed: Jan. 4, 2010

(65) Prior Publication Data
US 2010/0172798 A1    Jul. 8, 2010

Related U.S. Application Data

(63) Continuation of application No. PCT/EP2008/058473, filed on Jul. 2, 2008.

(30) Foreign Application Priority Data

Jul. 3, 2007   (EP) .................................... 07111622

(51) Int. Cl.
*G01N 21/77*  (2006.01)

(52) U.S. Cl. ........ 436/169; 436/164; 436/170; 422/119; 422/416; 422/503; 422/553; 422/420; 422/421; 422/422; 422/423; 422/424; 422/425; 422/426; 422/427; 422/428; 422/429; 422/68.1; 422/82.05; 422/82.06; 435/13; 435/283.1; 435/287.1; 435/287.7; 435/287.8; 435/287.9; 435/288.7

(58) Field of Classification Search .................... 422/66, 422/420, 421, 422, 423, 424, 425, 426, 427, 422/428, 429, 119, 416, 503, 553, 430, 400, 422/401, 68.1, 82.05, 82.06; 436/169, 170, 436/164; 435/13, 283.1, 287.1, 287.7, 287.8, 435/287.9, 288.7; 106/15.05, 31.13, 17, 106/18.2, 18.23, 18.24, 268, 272, 285, 38.2, 106/38.22, 38.3, 38.35; 2/901; 548/303.4, 548/314.1, 320.5; 264/319, 494, 96; 522/81; 523/200, 201, 205; 116/201, 206; 428/920, 428/921; 8/490, 115.59, 115.7, 182, 115.51, 8/115.6, 158, 495; 424/400, 401, 402, 403, 424/404, 405, 409, 411, 414, 416, 489, 486, 424/630, 63, 498, 500, 501, 502, 59, 76.3, 424/905, 907, 911, 913, 123, 124, 125, 136, 424/97; 514/725, 844, 963, 964, 965; 252/187.33, 252/608, 186.34, 408.1

See application file for complete search history.

(56) References Cited

U.S. PATENT DOCUMENTS

| | | | |
|---|---|---|---|
| 3,802,842 A * | 4/1974 | Lange et al. | .................. 436/169 |
| 5,846,837 A | 12/1998 | Thym et al. | |
| 6,036,919 A | 3/2000 | Thym et al. | |
| 6,271,040 B1 | 8/2001 | Bucchler | |
| 6,660,363 B1 | 12/2003 | Barthlott | |

(Continued)

FOREIGN PATENT DOCUMENTS

CA    2311496 A1    6/1999

(Continued)

*Primary Examiner* — Dennis M White
(74) *Attorney, Agent, or Firm* — Krieg DeVault LLP

(57) ABSTRACT

A method is provided for producing an analytical element comprising at least one test field for analyzing a liquid sample, wherein provision is made for a carrier on which a polymer fabric is arranged. At least one portion of the polymer fabric is irradiated with UV laser light and thereby hydrophobized.

10 Claims, 4 Drawing Sheets

U.S. PATENT DOCUMENTS

| | | |
|---|---|---|
| 2001/0024805 A1 | 9/2001 | Williams et al. |
| 2003/0013147 A1 | 1/2003 | Hildenbrand |
| 2005/0136217 A1 | 6/2005 | Barthlott et al. |
| 2006/0002816 A1 | 1/2006 | Zimmer et al. |
| 2006/0173380 A1 | 8/2006 | Hoenes et al. |
| 2006/0216817 A1 | 9/2006 | Hoenes et al. |
| 2006/0234269 A1 | 10/2006 | Asplund et al. |
| 2007/0110613 A1 | 5/2007 | Pachl et al. |

FOREIGN PATENT DOCUMENTS

| | | |
|---|---|---|
| CA | 2549143 A1 | 6/2005 |
| CA | 2506358 A1 | 11/2005 |
| DE | 10332488 A1 | 2/2005 |
| DE | 10343896 A1 | 4/2005 |
| EP | 0821233 A2 | 1/1998 |
| EP | 1291173 A1 | 3/2003 |
| EP | 1424040 A1 | 6/2004 |
| EP | 1593434 A2 | 11/2005 |
| EP | 1832874 A1 | 9/2007 |
| GB | 2350678 A | 12/2000 |
| WO | 96/04123 A1 | 2/1996 |
| WO | 97/02487 A1 | 1/1997 |
| WO | 98/43739 A2 | 10/1998 |
| WO | WO 9916964 A1 * | 4/1999 |
| WO | 00/58410 A1 | 10/2000 |
| WO | 00/58415 A1 | 10/2000 |
| WO | 2004/056269 A1 | 7/2004 |
| WO | 2005/054845 A1 | 6/2005 |

* cited by examiner

METHOD FOR THE PRODUCTION OF AN ANALYTICAL ELEMENT

CLAIM OF PRIORITY

The present application is a continuation application based on and claiming priority to PCT/EP2008/058473, filed Jul. 2, 2008, which is based on and claims the priority benefit of European Application No. EP 07111622.2, filed Jul. 3, 2007, each of which are hereby incorporated by reference in their respective entireties.

TECHNICAL FIELD OF THE INVENTION

The present application relates to an analytical element with at least one test field for analyzing a liquid sample, to a method for the production thereof, and more particularly to hydrophobization of test elements with a laser.

BACKGROUND

In order to analyze liquid samples, for example bodily fluids such as blood or urine, use is often made of analytical units in which the sample to be analyzed is located on a test field of an analytical element and possibly reacts with one or more reagents in the test field before being analyzed. The optical, in particular photometric, and electrochemical evaluations of analytical elements constitute the most common methods for quickly determining the concentration of analytes in samples. Analytical systems with analytical elements for analyzing samples are generally used in the field of chemical analysis, environmental analysis and, in particular, in the field of medical diagnostics. Analytical elements which are evaluated photometrically or electrochemically are very important, particularly in the field of blood glucose diagnostics from capillary blood.

There are different types of analytical elements. By way of example, substantially square platelets, which are also referred to as slides, are known and have a multilayered test field at their centers. Diagnostic analytical elements designed in the form of a strip are referred to as test strips. The prior art comprehensively describes analytical elements, for example in the documents CA 2311496 A1, U.S. Pat. No. 5,846,837 A or EP 0 821 233 A2, U.S. Pat. No. 6,036,919 A or WO 97/02487.

In capillary gap test elements, the sample liquid is moved in a transport channel (also referred to as a capillary channel or capillary gap) from a sample application location to a sample detection location, at a distance from said application location, using capillary forces in order to undergo a detection reaction at said sample detection location. Capillary gap test elements are known from, for example, CA 2549143 or US 2003/0013147 A1. The capillary channels such as microcapillaries often have an inner coating of hydrophilic and possibly hydrophobic materials. The liquid transport can be controlled by the hydrophilic and hydrophobic surface properties of the materials contacting the sample liquid.

Analytical tapes with a multiplicity of test fields which are wound up in a cassette and provided for use in an analytical unit are further analytical elements known from the prior art. Such cassettes and analytical tapes are described in, for example, the documents DE 103 32 488 A1, DE 103 43 896 A1, EP 1 424 040 A1, WO 2004/056269 A1 and CA 2506358 A1.

The present invention relates to arbitrarily-shaped analytical elements, such as strip-shaped test elements (e.g. strip-shaped capillary gap test elements) and analytical tapes.

Analytical elements generally have hydrophilic and hydrophobic regions. Herein, the terms "hydrophobic" and "hydrophilic" have the meanings which are generally understood in the art. A hydrophilic surface has a good wettability by water and a hydrophobic surface has a poor wettability by water. The wettability of a surface (and thus, for example, the flow velocity in a capillary having this surface) can be derived from the contact angle $\alpha$ formed between water (or a water-comprising sample) and the surface. If a liquid drop contacts a solid base, two extreme cases can occur. First, complete wetting can occur, in which the adhesion forces are greater than the cohesion forces. Therefore, the sample will spread on the surface of the solid body. Second, incomplete wetting can occur, in which the adhesion forces are (significantly) smaller than the cohesion forces. Therefore, the liquid will contract into a ball-shaped drop.

The wettability and hence, for example, the flow velocity of a liquid sample in a capillary increase as the contact angle $\alpha$ decreases. The filling time for filling a capillary per section increases exponentially with the contact angle. In the case of water-comprising samples, specifying the contact angle of water suffices to characterize the material-specific capillary properties. In this context, the term "hydrophobization" means a change of a surface which effects an increase in the contact angle formed between a liquid water-containing sample and the surface.

So-called "super-hydrophobic" surfaces should be mentioned as extreme cases of hydrophobic surfaces. Such surfaces are completely unwettable and so water drops completely roll off these surfaces. By way of example, such surfaces are used as self-cleaning surfaces.

In the prior art, hydrophilic or hydrophobic surface properties are generated by foils, for example, as a result of impregnating and/or coating processes which use auxiliary substances (e.g. detergents or waxes) suitable in this case. By way of example, hydrophilic or hydrophobic surfaces are produced in a targeted fashion in certain processes in semiconductor production, as a result of which, for example, certain structures can be obtained.

Hydrophilized or hydrophobized surfaces are often used in a targeted fashion also in a crossover field of semiconductor technology and biology, namely in the field of analysis using semiconductor chips (also referred to as "lab on a chip"), in order to produce so-called assays for certain target substances. In the prior art, examples of such chips with functionalized surfaces have been described. See, for example, US 2006/0234269 A1. In the process of making such chips, functionalized multilayered arrangements are used in coating technology which is conventional in semiconductor production, which multilayered arrangements are subsequently modified in a targeted fashion by the action of light, for example by being irradiated by a laser, and are partly ablated again in order to generate the desired structuring of the functionalization. However, such multilayered processes are technically complex, in many cases require complicated clean-room technology and expensive process technology, and are therefore usually unsuitable for mass production of analytical test elements for everyday use.

Other prior art references describe a diagnostic test carrier comprising a carrier layer with a detection layer, which comprises reagents required for determining an analyte in a liquid sample and arranged thereon, and a network which covers the detection layer, is larger than the detection layer and is attached to the detection layer. See, for example, EP 0 821 233 A2. Often, the network formed is hydrophilic, but not capillary-active on its own, and has an inert cover made of a sample-impermeable material which does not cover the sample application area. Such prior art test carriers are typically based on wettable networks which first of all as a whole constitute a possible sample application region. The actual sample application region is subsequently defined by, for example, covers in the form of adhesive tapes. However, such processes are generally complicated in practice, require a number of individual production steps, and in many cases for example only have limited suitability for mass production by means of a roll-to-roll method.

Other prior art references relate to a method for performing analyses, comprising the provision of a device for cultivating microorganisms. The device has an evaluation surface which has hydrophilic, liquid-retaining zones and a hydrophobic, elevated surface between these zones. The hydrophobic surface can be made to be hydrophobic using a number of methods. For example, a thin layer of acrylated silicone or another hydrophobic material can be applied to a polyethylene film which was made to be hydrophilic by a wetting agent being admixed thereto. See, for example, US 2001/0024805 A1.

Yet other prior art references relate to an analytical test element for determining an analyte in the liquid. The test element comprises an inert carrier, an application zone for sample material, a detection zone for determining the analyte and a channel or gap for transporting liquid from the application zone to the detection zone. The test element has a hydrophobically structured surface, at least in one region around the application zone. The structured hydrophobic surface with a lotus effect is produced by coating, saturating, spraying, coextrusion or injection molding. See, for example, WO 2005/054845 A1.

Again other prior art references describe methods for producing an analytical tape for liquid samples. In the process, a multiplicity of test elements are provided on a rollable transportation tape, are spaced apart in the direction of the tape, and are attached to the transportation tape as self-adhesive test labels. The test labels comprise a double-sided adhesive tape and a narrow detection film as a test field which is centered on the upper adhesive layer of the adhesive tape such that lateral adhesive strips of the adhesive layer remain uncovered. A cover layer formed as a fabric is applied thereon, which layer is wider than the detection film and the laterally protruding edges thereof are fixed by the lateral adhesive strips. The protruding edges of the cover layer outside of the detection film are hydrophobized by printing with a water-repellent impregnation and so only a central zone over the detection film can absorb a liquid sample and transport it to the detection film. See, for example, CA 2506358 A1.

The disadvantage of these methods for hydrophobization, known in the prior art, is that auxiliary substances (e.g. detergents, thermal transfer waxes) used for the coating have to be available for years with unchanging quality and with reliable supply conditions. Furthermore, troublesome interactions can occur if hydrophilic and hydrophobic reagents are used at the same time (e.g. interaction of a printed-on hydrophobic thermal transfer wax with a detergent coating of the printed fabric). Moreover, it is often impossible to produce sharp boundaries between hydrophilic and hydrophobically coated regions.

Furthermore, the prior art discloses the use of irradiation with electromagnetic radiation for hydrophobization. In some cases, a hydrophilic layer can be produced from a certain heat-sensitive composition and illuminated by IR radiation, as a result of which the illuminated regions of the layer become more hydrophobic. See, for example, EP 1291173 A1. In other cases, surfaces that have been made hydrophilic as a result of plasma treatments can be converted back into a hydrophobic surface by applying solvents, ultraviolet light or heat. See, for example, WO 98/43739 A2. However, in practice this type of conversion of hydrophilized surfaces into hydrophobic surfaces using the unspecific measures has disadvantages. By way of example, it is possible to ascertain that plasma-treated surfaces only temporarily maintain their high-energy, hydrophilic state. The surface energies are generally significantly increased and therefore not stable in the long-run. However, this means that the surfaces again return to their hydrophobic state over time and this can lead to a significant change in the test element properties. This low stability of the hydrophilization is generally also the reason why the conversion method can be effective, since it is very likely that the disclosed unspecific processes and ingredients such as heat, solvents and UV light would otherwise, in the case of a stably hydrophilized surface, not cause a change into a hydrophobic state.

Furthermore, the methods disclosed in the prior art are complex and costly because preparatory methods have to precede hydrophobization (coating with a heat-sensitive composition/hydrophilization by plasma treatment).

The object of the invention comprises avoiding the disadvantages of the prior art. In particular, it is also an object of the invention to provide a method for producing an analytical element by means of which surface regions of the analytical element can be hydrophobized in a cost-effective and flexible fashion. In particular, the method should be suitable for industrial production, in particular for a roll-to-roll method.

SUMMARY

This object and others that will be appreciated by a person of ordinary skill in the art have been achieved according to the embodiments of the present invention disclosed herein. In one embodiment, the present invention comprises a method for producing an analytical element with at least one test field for analyzing a liquid sample, wherein provision is made for a carrier on which a polymer fabric is arranged. At least one portion of the polymer fabric is irradiated with UV laser light and thereby hydrophobized.

In order to produce the analytical element, provision is made for a carrier on which a polymer fabric is arranged. By way of example, the carrier can have a planar shape, in particular be in the form of a strip or a tape, or be three-dimensional.

In this context, a test field is a field in which a liquid sample is analyzed. The test field is typically arranged on the carrier. By way of example, a test field is a detection zone designed such that certain components of the liquid sample, or the reaction thereof with reagents present in the detection zone, can be detected there. One example is a zone in which there is a detection reaction for glucose in a liquid sample (e.g. a blood sample) and photometric evaluation thereof.

Thus, the invention is based on hydrophobizing fabrics in contrast to, for example, the known semiconductor processes such as, for example, the method described in US 2006/0234269 A1 in which closed surfaces of liquid-guiding layers in chips, microchips or slides are hydrophobized by a targeted ablation of the coating. In contrast to such semiconductor techniques which usually require a batch-to-batch production, the inventive use of fabrics is substantially more suitable for mass production, in particular a roll-to-roll production.

However, in contrast to known methods which likewise utilize networks, such as, for example, the method described in EP 0 821 233 A2, covering techniques in which the structuring has to be generated by films using a masking process can be dispensed with.

The polymer fabric within the scope of the invention is a fabric made of polymer threads or a nonwoven made of polymer fibers. The polymer fabric can comprise a polymer selected from the group comprising polyester, polyamide, polypropylene and polyacrylonitrile.

The polymer fabric arranged on the carrier can be hydrophilic or hydrophilized (prior to irradiation with UV laser light) and is used in portions on the analytical element (which are not irradiated by UV laser light) for receiving and/or transporting the liquid sample. It is suitable for the polymer fabric to be in direct contact with the test field; for example, said polymer fabric wholly or partly covers the test field such that it can receive a liquid sample in the non-hydrophobized regions and transfer said sample to the test field. However, the polymer fabric itself can also be used as a test field for analyzing a liquid sample in at least one portion and can, for example, comprise reagents in this at least one portion for detecting an analyte in the liquid sample. The polymer fabric can have a detergent for spreading the sample on the fabric. The detergent need not itself have reagents for detecting an analyte. These reagents are generally located in a detection film. The liquid sample can be essentially any water-comprising sample, e.g. plasma, blood, interstitial fluid, urine, saliva, sweat, or a sample from water analysis (in particular old water).

According to the invention, at least one portion of the polymer fabric is irradiated with UV laser light and thereby hydrophobized in the irradiated region. UV laser light is the light emitted by a laser at a wavelength in the range of 1 nm to 380 nm. Suitable wavelengths of the UV laser light used in the method according to the present invention have been found to include about 248 nm, about 266 nm and about 355 nm. The UV laser light can be provided by diode-pumped solid state lasers or excimer lasers. At least one portion of the polymer fabric is irradiated with UV laser light in a targeted fashion. In this context, targeted means that no masks or the like are used but that at least one laser beam is focused onto the portion using suitable optical components and said beam passes over (scans) this portion, and therefore a spatially resolved hydrophobization of the polymer fabric is achieved. However, alternatively, or additionally, a mask method can also be used in the irradiation with laser light, for example a mask illumination method using an UV excimer laser.

In contrast to the methods known from the prior art, a specific treatment is therefore performed using the UV laser light rather than unspecific light irradiation. This specific treatment, which can be performed in a spatially resolved fashion, can transform chemically and long-term stable hydrophilic surfaces into a new, hydrophobic state by means of specific UV laser radiation.

The portion of the polymer fabric hydrophobized using UV laser light, or a completely hydrophobized polymer fabric on the analytical element, can for example be used to slow or stop the flow of the liquid sample or to prevent wetting of the portion by the liquid sample (e.g. during sample application). It is possible for a hydrophilic/hydrophobic pattern to be generated by hydrophobizing one or more portions of a provided hydrophilic polymer fabric.

As a result of the irradiation with the UV laser light, the polymer fabric is structured in the region irradiated with UV laser light, that is to say the surface structuring is changed by the laser light. In particular, the polymer surface of the polymer fabric can be roughened by the irradiation with laser light. A pulsed laser can be used for structuring, wherein the pulsed laser beam scans the portion of the polymer surface and the polymer surface is structured by the laser pulses impinging on the polymer surface, spaced apart at a certain distance from one another. A suitable choice of laser parameters (wavelength, power, pulse rate, etc.) affords the possibility of generating microstructures in a targeted fashion, which microstructures cause hydrophobic properties. As a result of the laser light, molten, round structures (bumps and recesses) are produced on the polymer surface of the threads or fibers of the polymer fabric, the average spacing of which structures (for example from recess to recess) is referred to by the term "hatch distance".

By way of example, portions of the polymer surface of the polymer fabric can be modified by such a structuring such that they have the so-called "lotus effect". By way of example, this effect is described in WO 96/04123 A1, WO 00/58410 A1 or WO 00/58415 A1. Such a surface has bumps and recesses, wherein the distance between the bumps lies in the range of between about 0.1 and about 200 µm and the height of the bumps in the range of about 0.1 to about 100 µm, and the bumps are hydrophobic.

Furthermore, the portion of the polymer fabric can be structured by the UV laser light such that impurities, such as air molecules, can be included in the generated recesses, as a result of which the polymer surface is hydrophobized.

The advantage of the method according to the invention lies in the fact that there is a direct interaction between the laser light and the polymer fabric during the irradiation with UV laser light, which direct interaction causes the desired hydrophobic effect. Additional auxiliary reagents are not required. Complicated production method steps (impregnations, saturations, plasma treatments) for preparing the hydrophobization are dispensed with. The irradiation with UV laser light allows substantial freedom in the design of the geometry of hydrophobic regions. The UV laser treatment is well-adjustable and controllable during online operation.

In accordance with one embodiment of the present invention, the polymer fabric is a monophilic fabric comprising threads which largely run parallel or perpendicular to one another, wherein the threads running parallel to one another have a spacing of between about 1 µm and about 0.5 mm to one another. Other suitable spacing can be between about 0.1 and about 200 µm. A monophilic fabric is a fabric in which individual threads are interweaved in the longitudinal and transverse directions. Monophilic fabrics are more defined than conventional types of fabric, for example in respect of their pore size, the homogeneity, the air permeability or other properties. Typical mesh apertures can for example lie between about 105 and about 285 micrometers, typical thread diameters between about 42 and about 145 micrometers and typical fabric thicknesses between about 63 and about 260 micrometers.

The processing of fabrics, as proposed within the scope of the present invention, generally differs significantly from the functionalization of closed surfaces as is known, for example, from semiconductor technology, or from the processing of films. While semiconductor processes or the functionalization of films are usually performed using coating processes, for example using spin-coating or coating with a knife coater, such techniques cannot be used for processing fabric. Therefore, provision can be made for a carrier in the production method according to the invention, on which carrier the polymer fabric is coated with a detergent. In the process, the detergent typically coats the individual threads or fibers of the polymer fabric and so the interfacial surface tension between the liquid sample and the surface of the polymer fabric is lowered. By way of example, in contrast to the above-described semiconductor-typical coating technologies, the detergent can be applied to the polymer fabric by means of a saturation process.

The detergent can comprise at least one detergent selected from the group comprising sodium dioctylsulfosuccinate (DONS), Mega-8® (octanoyl-N-methylglucamide) and nonylphenol ethoxylates, in particular polyethylene glycol [4-(1,1,3,3-tetramethylbutyl)phenyl]ether (Triton®). The detergent, in particular the DONS, can for example be applied to a polyester fabric as a solid layer by saturating the fabric with DONS dissolved in ethanol and subsequent drying.

By way of example, a start can be made with a hydrophilic, hydrophobic or already at least partly hydrophobized polymer fabric. This fabric can then be saturated with the detergent, for example by pulling the fabric through an appropriate bath with the detergent, for example a DONS solution. Other saturation techniques are also known and can be utilized, for example spraying techniques or the like. As a result of this saturation with the detergent, the fabric becomes hydrophilic, or the hydrophilicity of the fabric is increased.

In contrast to the batch processes known from semiconductor technology, this saturation can also be effected on an industrial scale, for example in a roll-to-roll process. A combination with a laser process is also possible on an industrial scale. Thus, the invention provides a combination of areal application methods onto fabric, such as, for example, saturation, and spatially resolved methods in the form of laser structurings. All of these steps can be implemented as roll-to-roll processes.

Subsequently, the described irradiation using UV laser light can be effected in order to once again in a targeted fashion hydrophobize the portion of the fabric hydrophilized in this fashion. In accordance with another embodiment of the present invention, the detergent is at least partly removed by the UV laser light in the portion of the polymer fabric irradiated with UV laser light. Here, the hydrophobization caused by UV laser irradiation is based on removing the detergent from the polymer fabric, in particular by ablation, and possibly also on the structuring of the surface of the polymer fabric.

It was found that the renewed hydrophobization of the portion of the fabric saturated with the detergent can in particular be effected such that a super-hydrophobization occurs. Thus, in many cases it is not only the detergent, in particular the DONS, that is ablated from the fabric surface, but action is also effected on the surface structure of the threads of the polymer fabric, as illustrated. However, such a super-hydrophobization, that is to say such a complete unwettability, is an extremely desirable property, particularly in the case of analytical test elements. Thus, such a super-hydrophobization may be required for a blood barrier property of a test field. In this respect, normal hydrophobicity is insufficient in many cases.

The targeted UV laser irradiation of a polymer fabric coated with a detergent has a multiplicity of advantages over, for example, the printing of a hydrophobic substance (in particular, the printing of a PET fabric impregnated with DONS using thermal transfer wax) onto such a polymer fabric coated with a detergent known from the prior art. In the known thermal transfer wax application, a wax mixture applied to a film is liquefied by heat and printed onto the PET fabric impregnated with DONS. In the process, the hydrophilic DONS mixes with the hydrophobic wax mixture. In this case, a precondition for generating an operational hydrophobic barrier is a precise setting of the mixing ratio of detergent (DONS) and wax. It is impossible to produce defined boundaries between hydrophobized regions with wax and hydrophilic regions without wax; rather, transition regions are created. UV laser irradiation avoids these disadvantages. There is no interaction between hydrophilic and hydrophobic reagents. There is a multiplicity of possibilities for the design of hydrophilic and hydrophobic regions on analytical elements. Furthermore, the hydrophobic property generated by the UV laser treatment is very stable for a period of at least 6 months.

One embodiment variant of the method according to the invention comprises the analytical element being a test element for determining an analyte in a liquid sample, which test element comprises an application zone for the liquid sample, wherein the polymer fabric is irradiated with UV laser light in a region around the application zone and thereby hydrophobized. Here, the test element can comprise a test strip or a test label arranged on an analytical tape.

In this context, an application zone is a region of the analytical element provided for receiving a liquid sample which is transported, mixed, separated, contacted by reagents and/or processed and analyzed in a different fashion on the analytical element.

The hydrophobization in the region around the application zone in which, for example, the opening of a capillary channel or a hydrophilic polymer tissue is located clearly delimits the application zone. When the liquid sample (e.g. blood) is applied to the application zone, excess sample liquid is either taken in by the application zone (for example, soaked up into a capillary channel or transported on to an analytical zone by means of a hydrophilic polymer fabric) or drips off the hydrophobized region and so only the application zone is wetted and contamination of the surroundings of the application zone of the analytical element and of a measuring instrument holding the analytical element is avoided.

In accordance with another embodiment of the present invention, in order to produce a test element, a detection film is applied to the carrier whilst keeping edges uncovered, the detection film is covered by the polymer fabric, with the polymer fabric projecting beyond the detection film in lateral regions and covering the uncovered edges of the carrier, and the polymer fabric is hydrophobized in the lateral regions by irradiation with UV laser light. The carrier used in this case can be an adhesive tape, such as a double-sided adhesive tape, by means of which the test element is transferred onto a transportation tape as a self-adhesive test label. The design of the analytical element in one embodiment corresponds to the analytical tape described in CA 2506358 A1, the difference being that the polymer fabric outside of the detection film is not printed with a water-repellent impregnation but rather is hydrophobized in the lateral regions by being irradiated with UV laser light. Therefore, reference is expressly made to CA 2506358 A1.

The invention furthermore relates to an analytical element which was produced in accordance with the method according to the invention and comprises at least one test field for analyzing a liquid sample, wherein the analytical element comprises a carrier on which a polymer fabric is arranged. At least one portion of the polymer fabric is hydrophobized by irradiation with UV laser light.

In accordance with yet another embodiment variant, the analytical element according to the invention comprises an analytical tape with a multiplicity of test elements spaced apart in the direction of the tape.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
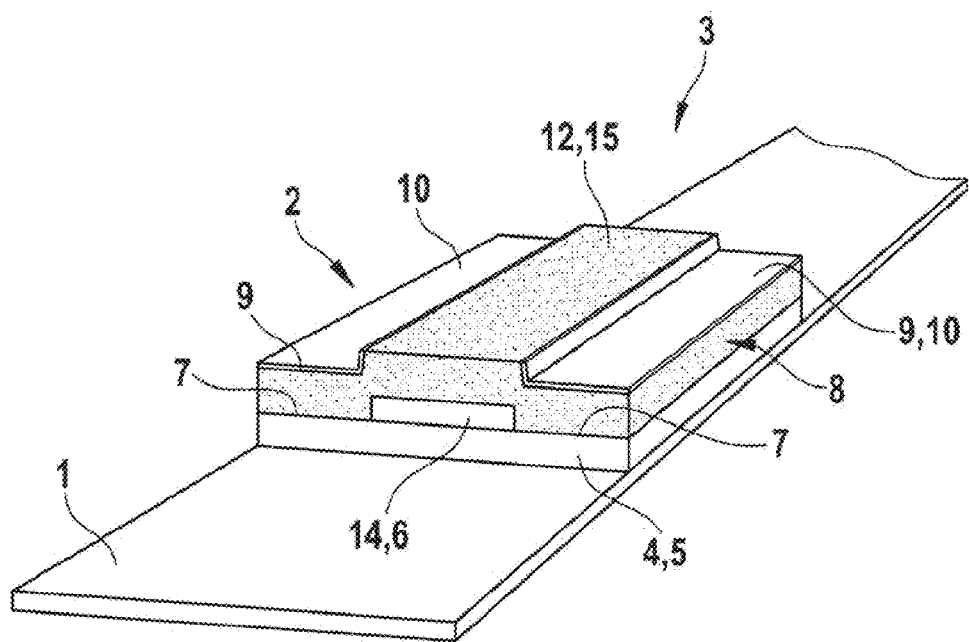
FIG. 1 schematically shows a perspective view of an analytical element according to the prior art in the form of an analytical tape.

FIG. 1 shows an analytical element known from the prior art. The analytical element is an analytical tape 3, a section of which is illustrated in FIG. 1, which tape comprises a rollable transportation tape 1 and, arranged thereon, a multiplicity of test elements 2 spaced apart in the direction of the tape. The test elements 2 (only one of which is illustrated in FIG. 1) are for example provided for analyzing bodily fluids, in particular blood.

The test element 2 has a multilayered design as a self-adhesive test label. A double-sided adhesive tape 5 is used as a carrier 4 for the test element 2. A narrow detection film 6 is adhesively attached centrally on the upper adhesive layer of the double-sided adhesive tape 5 and so lateral edges 7 are kept uncovered on the carrier. The detection film 6 is covered by a polymer fabric 8. The polymer fabric 8 is wider than the detection film 6 and so the polymer fabric 8 projects beyond the detection film 6 in lateral regions 9. Thus, the polymer fabric 8 is fixed in the lateral regions 9 by the edges 7 of the adhesive tape 5.

In the prior art, the lateral regions 9 have a hydrophobic thermal transfer wax 10 as a water-repellent impregnation printed thereon and so only the central test field (detection zone 14) can soak up and, to a limited extent, spread the liquid sample to be applied. The polymer fabric 8 comprises a detergent which mixes with the thermal transfer wax 10 when the latter is used for impregnation. In the process, a critical balance between thermal transfer wax 10 and detergent has to be maintained in order to set the desired hydrophobicity of the lateral regions 9.

Figure 2:
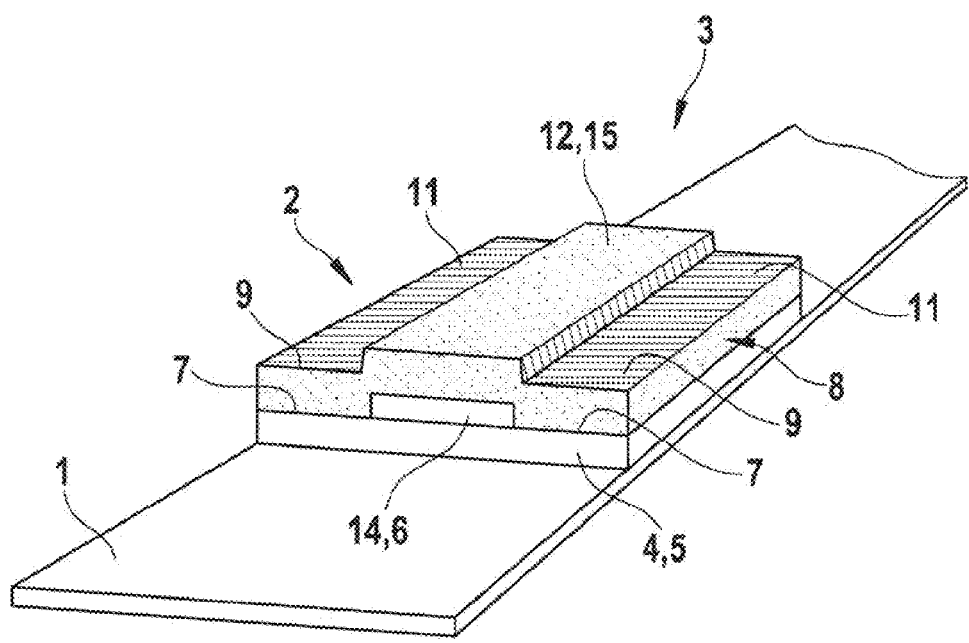
FIG. 2 schematically shows a perspective view of an analytical element according to the invention in the form of an analytical tape, produced in accordance with the method according to the invention.

FIG. 2 shows an analytical element according to the invention in the form of an analytical tape, produced in accordance with the method according to the invention.

The analytical element essentially has the same design as the analytical element according to FIG. 1. The same reference signs refer to the same components of this analytical tape 3. However, unlike the analytical element in accordance with FIG. 1, the analytical element according to the invention in accordance with FIG. 2 does not have printing made of thermal transfer wax. Instead, the lateral regions 9 of the polymer fabric 8 impregnated by the detergent are hydrophobized or even super-hydrophobized by irradiation with UV laser light. The function of these hydrophobic regions 11 arranged on both sides is to allow localized sample application onto the polymer fabric 12 which is provided as an application zone 15, is arranged centrally and is designed to be hydrophilic, without the liquid sample contaminating the surroundings, which sample does not wet the lateral hydrophobic regions 11, or does not wet said regions very well.

Figure 3A:
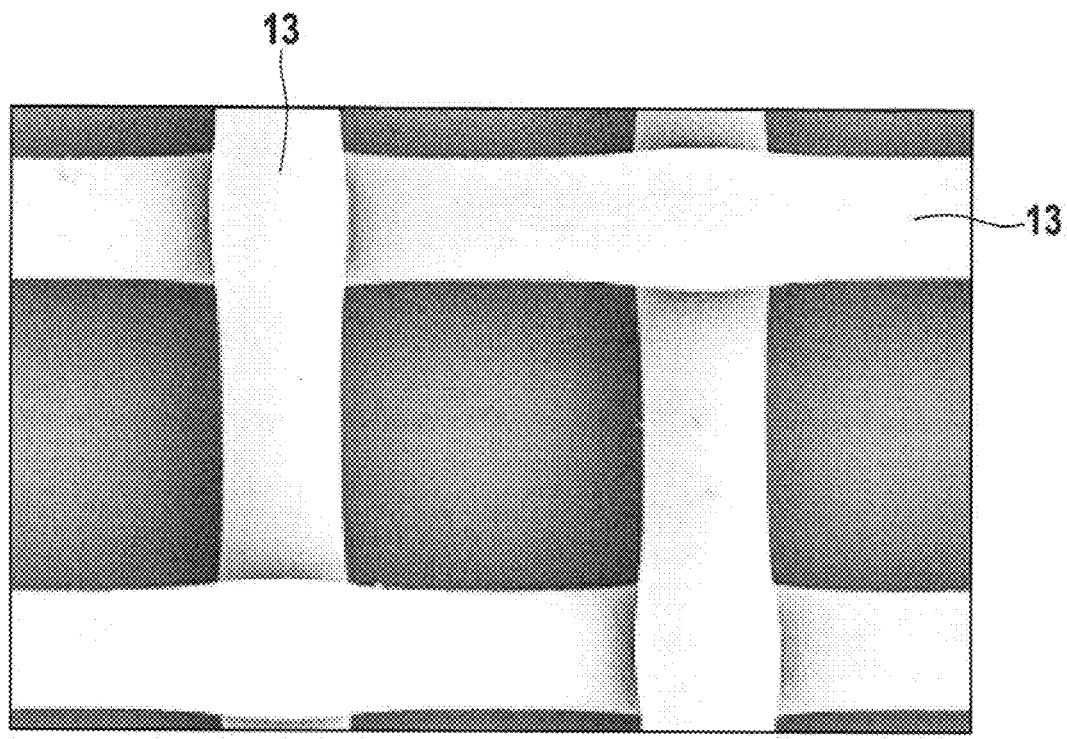
FIGS. 3A and 3B show enlarged views of a polymer fabric hydrophobized by UV laser irradiation before the laser treatment (FIG. 3A) and after the laser treatment (FIG. 3B).
Figure 3B:
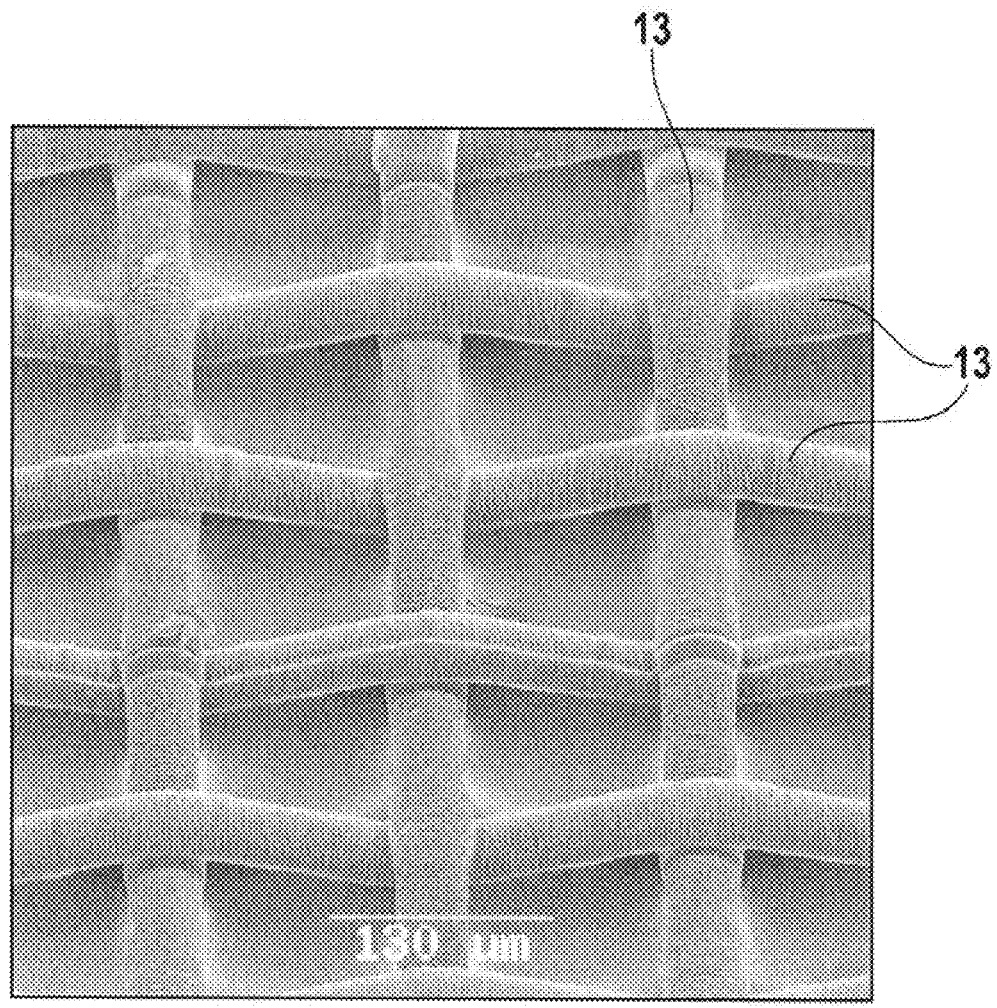

FIGS. 3A and 3B show enlarged views of a polymer fabric hydrophobized by UV laser irradiation. Here, FIG. 3A shows a polymer fabric before the laser treatment, whereas FIG. 3B shows the fabric after the laser treatment. By comparing the two images it becomes apparent that the laser treatment generates a surface roughness which affects the wetting properties of the surfaces.

The polymer fabric is a polyester fabric. It is a monophilic fabric comprising threads 13 which largely run parallel or perpendicular to one another, wherein the threads 13 running parallel to one another a spacing of approximately 80-120 µm.

The laser irradiation was performed using different UV laser types. Thus, an excimer laser with a wavelength of 248 nm, a frequency of 100 Hz, a pulse energy of 7 mJ and a spot size of 400 micrometers was used. In three experiments, the number of pulses was varied between 10 pulses, 15 pulses and 20 pulses. Furthermore, a 4-f diode laser with a wavelength of 266 nm was used. The diode laser was likewise operated in a pulsed mode, with a pulse frequency of 30 kHz and a pulse energy of 10 microjoule. The spot size was 18 micrometers.

In this case, the polymer fabric was impregnated using DONS in accordance with the above description. The laser treatment generated a fine structuring on the fabric threads in conjunction with a local removal of the DONS. This structuring can clearly be seen in FIG. 3B in the form of a ribbing of the threads 13. In the process, the contact angle changed in the direction toward the super-hydrophobic region, that is to say into a region with a standing drop. In general, the hydrophobic properties, or the hydrophobic functions, of a fabric treated in this fashion by a UV laser can be detected in tests with blood and/or a saline. By way of example, the fabrics treated according to the invention displayed at least equal or increased hydrophobic properties compared to fabrics hydrophobized in a conventional fashion, for example by using waxes, up to standing, spherically-shaped drops on the fabric treated according to the invention.

Figure 4:
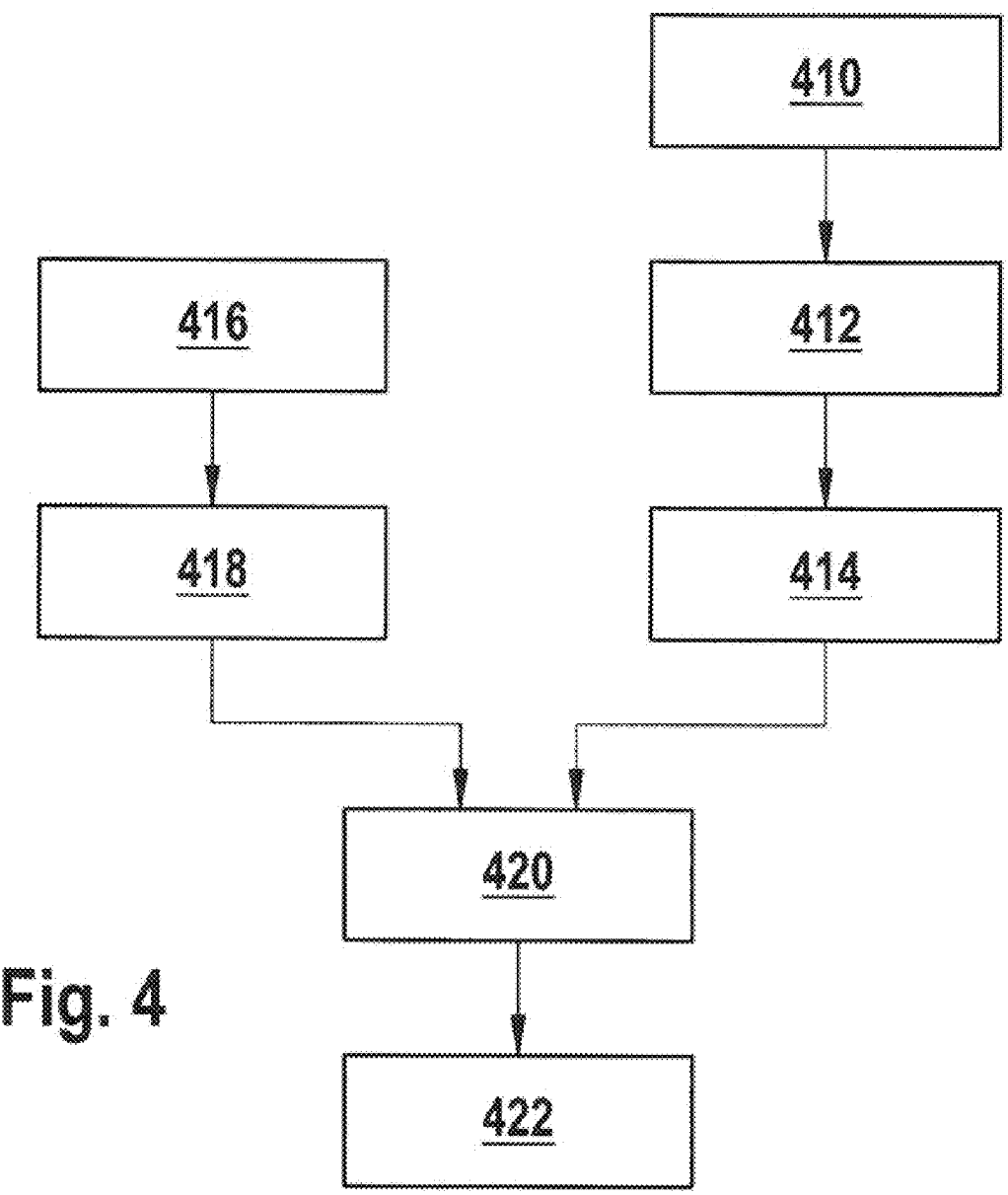
FIG. 4 shows a schematic flowchart of an exemplary embodiment of a production method according to the invention.

FIG. 4 illustrates a schematic flowchart of an exemplary embodiment of a production method according to the invention for producing a test element. The illustrated method steps can be complemented by additional method steps not illustrated in FIG. 4. Furthermore, although the illustrated sequence is useful, it is not necessarily required and, for example, individual or a number of method steps can also be combined, repeated or performed in parallel. By way of example, the method can be used for producing the test element 2 illustrated in FIG. 2 and so reference can be made, for example, to the description of this figure for the individual components and the function thereof.

A transportation tape 1 is provided in a first method step 410. Then, the carrier 4 and the double-sided adhesive tape 5 are applied to this transportation tape 1 in a subsequent method step 412. The test field 14 in the form of the detection film 6 can then be applied to the transportation tape 1 prepared in this fashion, or to the carrier 4 and the adhesive layer 5, in a method step 414.

In parallel with this, the polymer fabric 8 can be provided in a method step 416. This polymer fabric 8 is then saturated in method step 418 with a detergent, for example DONS in accordance with the description above.

In method step 420, the polymer fabric 8 saturated in this fashion is applied to the test element prepared in method step 414 such that this polymer fabric 8 covers the carrier 4 and the detection film 6, as can be seen in FIG. 2.

Subsequently, in method step 422, the test element 2 prepared in this fashion is subjected to a UV laser treatment in the regions referred to by reference numeral 11 in FIG. 2. During this UV laser treatment in step 422, the detergent is removed from the polymer fabric 8 in the regions 11 and, additionally, the surface of this polymer fabric 8 is modified, as demonstrated in the preceding FIGS. 3A and 3B. This produces the hydrophobic regions 11 which in most cases even exhibit super-hydrophobicity, particularly when using DONS and the UV laser treatment. In this fashion, the centrally arranged polymer fabric 12 becomes the delimiting surface for the application of aqueous liquid samples, such as, for example, blood samples. Hence, the super-hydrophobic regions 11 delimit the test field or the detection zone 14 effectively.

Reference is made to the fact that alternative production methods to the production method illustrated in FIG. 4 are also possible. Thus, it is possible, for example, to firstly apply the polymer fabric 8 saturated with the detergent onto the carrier 4 with the detection film 6 applied thereto, and then to cut out corresponding fields from the carrier coated in this fashion, which are only then applied to the transportation tape 1, for example by adhesive bonding. The UV laser treatment can be performed before or after the application onto the transportation tape 1. In principle, other production methods are also feasible.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for producing an analytical element with at least one test field for analyzing a liquid sample, comprising providing a carrier on which a polymer fabric is arranged, coating the polymer fabric with a detergent, irradiating at least one portion of the polymer fabric with UV laser light to thereby hydrophobize the at least one portion, and at least partly removing the detergent at the at least one portion of the polymer fabric by the irradiating with UV laser light.

2. The method as claimed in claim 1, wherein the polymer fabric is a monophilic fabric comprising threads which run generally parallel or generally perpendicular to one another, wherein the threads are spaced apart by between about 1 μm and about 0.5 mm.

3. The method as claimed in claim 1, wherein the detergent comprises at least one detergent selected from the group consisting of sodium dioctylsulfosuccinate (DONS), octanoyl-N-methylglucamide and polyethylene glycol [4-(1,1,3,3-tetramethylbutyl)phenyl]ether.

4. The method as claimed in claim 1, wherein the at least one portion of the polymer fabric where the detergent is at least partly removed by UV laser light is super-hydrophobized.

5. The method as claimed in claim 1, wherein providing the analytical element comprises producing a test element for determining an analyte in a liquid sample, the test element comprising an application zone for the liquid sample, wherein the irradiating of the at least one portion of the polymer fabric with UV laser light is performed in a region around the application zone.

6. The method as claimed in claim 5, wherein producing the test element comprises applying a detection film to the carrier whilst keeping edges of the carrier uncovered, the detection film being covered by the polymer fabric, the polymer fabric projecting beyond the detection film in lateral regions and covering the uncovered edges of the carrier, wherein the irradiating of the at least one portion of the polymer fabric with UV laser light is also performed in the lateral regions.

7. The method as claimed in claim 6, wherein the carrier comprises an adhesive tape by means of which the test element is transferred onto a transportation tape as a self-adhesive test label.

8. The method as claimed in claim 1, wherein the method for producing the analytical test element generally comprises a roll-to-roll process.

9. An analytical element produced by the method as claimed in claim 1, comprising at least one test field for analyzing a liquid sample, wherein the analytical element comprises a carrier on which a polymer fabric is arranged, and wherein at least one portion of the polymer fabric is hydrophobized by irradiation with UV laser light.

10. The analytical element as claimed in claim 9, wherein the analytical element comprises an analytical tape with a multiplicity of test elements spaced apart in the direction of the tape.

* * * * *